United States Patent [19]

Mimoun et al.

[11] Patent Number: 4,529,824
[45] Date of Patent: Jul. 16, 1985

[54] PEROXIDIC COMPLEXES OF VANADIUM, NIOBIUM AND TANTALUM, USED AS REACTANTS AND AS CATALYSTS FOR OLEFINS EPOXIDATION AND HYDROCARBONS HYDROXYLATION

[75] Inventors: Hubert Mimoun, Rueil-Malmaison; Lucien Saussine, Chatou; Erick Daire, Rueil-Malmaison; Alain Robine, Clamart; Jacques G. de Luzinais, Rueil-Malmaison, all of France

[73] Assignee: Institut Francais du Petrole, Rueil-Malmaison, France

[21] Appl. No.: 506,480

[22] Filed: Jun. 21, 1983

[30] Foreign Application Priority Data

Jun. 21, 1982 [FR] France .................................. 82 10938

[51] Int. Cl.$^3$ ....................... C07C 37/60; C07C 39/04
[52] U.S. Cl. ..................................... 568/803; 568/741; 568/771
[58] Field of Search ....................... 568/803, 741, 771

[56] References Cited

U.S. PATENT DOCUMENTS

| | | | |
|---|---|---|---|
| 2,395,633 | 2/1946 | Milas | 568/803 |
| 2,437,648 | 3/1948 | Milas | 568/803 |
| 3,488,395 | 1/1970 | Hooper. | |
| 3,662,006 | 5/1972 | Maisse et al. | 568/803 |

OTHER PUBLICATIONS

Funahashi et al. "Inorganic Chemistry" vol. 16, (1977) pp. 1349–1353.
Milas, "J. Amer. Chem. Soc." vol. 59 (1937) pp. 2342–2344.

*Primary Examiner*—Werren B. Lone
*Attorney, Agent, or Firm*—Millen & White

[57] ABSTRACT

Peroxidic complexes of vanadium, niobium or tantalum, wherein the metal is linked to an oxygen molecule carrying two negative charges, are used either as reactants for the oxidation of olefinic substrates or hydrocarbons, or as hydrocarbons oxidation catalysts, particularly for converting olefinic compounds to epoxides or aliphatic or aromatic hydrocarbons to the corresponding alcohols or phenols.

18 Claims, No Drawings

PEROXIDIC COMPLEXES OF VANADIUM, NIOBIUM AND TANTALUM, USED AS REACTANTS AND AS CATALYSTS FOR OLEFINS EPOXIDATION AND HYDROCARBONS HYDROXYLATION

The present invention concerns the use of peroxidic complexes of vanadium, niobium and tantalum as reactants and as hydrocarbons oxidation catalysts, particularly for the conversions of olefinic compounds to epoxides and the conversion of aliphatic or aromatic hydrocarbons to the corresponding alcohols and/or phenols. The invention also concerns a preferred mode of preparation of these complexes.

The term peroxidic complexes designates metal compounds wherein the metal is linked to an oxygen molecule carrying two negative charges ($O_2{}^{2-}$), these complexes being optionally of the peroxide type (Form A) or hydroperoxide (Form B)

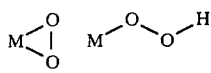

A    B

The complexes conform with one of the following formulas I to IV:

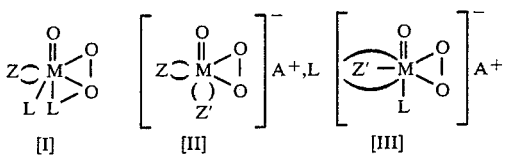

In the formulas [I] to [IV], M is vanadium, niobium or tantalum, Z and Z', identical or different, each represent an anion or a monoanionic mono or bidentate group, Z" is a dianion or a dianonic tridentate group, L and L', identical or different, each represent a molecule of water or a mono or bidentate ligand with electrodonor properties, and $A^+$ is a proton or a group with a positive charge.

I DEFINITION OF Z, Z', Z", L, L' and A

1/- In the above mentioned complexes [I] and [II], Z and Z' are preferably mono or polyaromatic nitrogenous heterocyclic compounds having at least one carboxylic group vicinal to the nitrogen atom, substituted or not with one or more Y groups, wherein Y is an alkyl, aryl, alkyloxy, aryloxy radical or a $NO_2$ group, or a halogen, a carboxylic group, an ester, a carboxyamide, a hydroxyl, these Y groups being at any one or at several positions of the one or more separate or joined aromatic rings, according, for example, to the following representative formula:

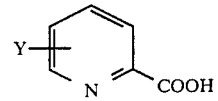

Non-limitative examples of such mono or polyaromatic compounds are 2-pyridine carboxylic (or picolinic) acid, 2,3-; 2,4-; 2,5-pyridine dicarboxylic acid, 2- or 8-quinoline carboxylic acid, 1 or 3-isoquinoline carboxylic acid, 3,4,5 and 6-chloro, bromo, nitro, hydroxy, methyl, ethyl, propyl, butyl, phenyl picolinic acids, 2,3-, 2,4-, 2-5- or 2,6-pyridine dicarboxylic mono alkyl or aryl esters, 1,2-, 1,3-, or 1,4-pyrazine-6-carboxylic acids.

There can also be used as bidentate anionic ligands Z and Z', the N-oxides of mono or polyaromatic nitrogenous heterocyclic compounds having a carboxylic group vicinal to the nitrogen atom, substituted or not with one or more Y groups selected from the alky, aryl, alkyloxy, aryloxy, nitro, halogen, carboxylic, carboxyamide, hydroxyl groups, these Y groups being in any one or several positions of the one or more selected aromatic rings, according to the formula:

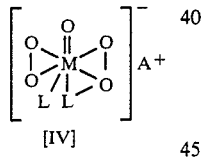

Non-limitative examples are picolinic acid N-oxide, 2- or 8-quinoline carboxylic acid N-oxide, 2,3-; 2,4- or 2,5-pyridine dicarboxylic acid N-oxide.

2/ In formula III, Z" is preferably a tridentate dianionic ligand derivating from 2,6-pyridine dicarboxylic (or dipicolinic) acid, mono, di or trisubstituted with one or more Y groups, according to the formula:

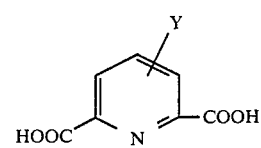

wherein Y is an alkyl, aryl, alkyloxy, aryloxy, halogen, nitro, carboxylic, carboxyamide, hydroxyl group.

3/ In complexes [I] to [IV], L and L', identical or different, represent a molecule of water, an alcohol such as methanol or a mono or bidentate ligand (or still form together a bidentate ligand) with electrodonor properties, said ligand being selected from the group consisting of:

(a) an aromatic amine comprising one or more optionally joined benzene rings and one or more nitrogen atoms per ring. Non-limitative examples are pyridine, quinoline, acridine, 2-, 3- and 4-picolines, collidine, 4-dimethylaminopyridine, picolinic acid, methyl picolinate, nicotinic acid, isonicotinic acid, N-methyl imidazole, 2,2'-bipyridine and orthophenantroline, (b) linear or cyclic tertiary amide of the formula $R''_1 CO N R''_2 R''_3$ wherein $R''_1$, $R''_2$ and $R''_3$, idential or different, each represent a hydrocarbon radical comprising from 1 to 20 carbon atoms per molecule or at least two or these radicals $R''_1$, $R''_2$ and $R''_3$ from together a ring containing 4 to 30 carbon atoms per molecule. Non-limitative examples are dimethyl formamide, dimethylacetamide, N,N-dimethyl benzamide, N,N-diethylnicotinamide, bis N,N-diethylphthalimide, N-acetyl morpholine, N-benzoylpiperidine, N-formyl piperidine, N-acetyl piperidine, N-methylpyrrolidone, N-ethylpyrrolidone, N-phenyl pyrrolidone, N-methyl valerolactame, N-methyl caprolactame, N,N-diethyl picolinamide, (c) a phosphoramide of the formula $(R'''_1 R'''_2 N)_3 PO$ wherein $R'''_1$ and $R'''_2$, identical or different, each represent a hydrocarbon radical comprising from 1 to 20 carbon atoms per molecule. Non-limitative examples are hexamethyl phosphorotriamide, hexaethyl phosphorotriamide and octamethylpyrophosphoramide, (d) an oxide of an aliphatic or aromatic amine such as trimethyl amine oxide, N-methylmorpholine oxide, pyridine oxide, 2-, 3- and 4-picoline oxides, quinoline oxide, 2,2'-bipyridine N-oxide, (e) an oxide of phosphine, arsine or stibine such as triphenylphosphine oxide, triphenyl arsine oxide, triphenylstibine oxide, trimethyl phosphine oxide, methyl diphenyl phosphine oxide, diethylphenyl phosphine oxide and trimorpholinophosphine oxide.

4/ In complexes II, III IV, A represents a proton or a cation or cationic group selected from the group consisting, for example, of:

(a) an alkali metal such as lithium, sodium, potassium, rubidium or cesium, (b) a quaternary ammonium group of the general formula $N R R' R'' R'''$, wherein R, R', R'' and R''', identical or diffenrent, are each either a hydrogen atom or an alkyl, aryl, aralkyl or alkylaryl hydrocarbon radical comprising from 1 to 20 carbon atoms per molecule. Non-limitative examples are the ammonium cation, the tetramethyl, tetraethyl, tetrapropyl, tetrabutyl, tetraphenyl ammonium cations, the methyltriphenyl, benzyltrimethyl, benzyltributyl, benzyltriphenyl, cetyltrimethyl, cetyltriphenyl ammonium cations, (c) a quaternary phosphonium group of the general formula $P R R' R'' R'''$, wherein R, R', R''', identical or different, are each either a hydrogen atom or an alkyl, aryl, aralkyl or alkylaryl hydrocarbon radical comprising from 1 to 20 carbon atoms per molecule. Non-limitative examples are tetramethyl, tetraethyl, tetrapropyl, tetrabutyl, tetraphenyl phosphonium cations, methyltributyl, methyltriethyl, methyltriphenyl, butyltriphenyl, ethyltriphenyl phosphonium cations, (d) a quaternary arsonium group of the general formula $As R R' R'' R'''$, wherein R, R', R'', R''', identical or different are each an alkyl, aryl, aralkyl or alkylaryl hydrocarbon radical comprising from 1 to 20 carbon atoms per molecule. Non-limitative examples are tetramethyl, tetraethyl, tetrapropyl, tetrabutyl and tetraphenylarsonium cations.

II PREPARATION OF THE COMPLEXES

The preferred preparations of the complexes, which will be described more in detail in the examples, may be effected in different manners. They generally consist of reacting one salt or complex of vanadium, niobium or tantalum with hydrogen peroxide in the presence of ligands Z H, Z' H and Z" H, precursors of the above mentioned anions, Z, Z' and Z", in the presence or the absence of electrodonor ligands L and L' and in the presence or absence of salts of the formula $A^+X^-$ (precursors of cations or cationic groups $A^+$) wherein $X^-$ is an anion such, for example, as chlorine, bromine, iodine, a carboxylate, a nitrate, a perchlorate, a cyanide, etc...

As vanadium precursor, there can be selected, for example, vanadic anhydride $V_2O_5$, V (acetylacetonate)$_3$ or VO (acetylacetonate)$_2$, a vanadyl alcoholate VO $(OR)_3$, vanadyl sulfate $VOSO_4$, vanadyl nitrate VO $(NO_3)_3$, vanadyl chloride VO $Cl_3$ or a vanadyl alkyldithiocarbamate VO $(R_2NCS_2)_3$.

As niobium and tantalum precursors, there can be selected, for example, the oxides $Nb_2O_5$ and $Ta_2O_5$, the chlorides Nb $Cl_5$ and Ta $Cl_5$, the oxychlorides $NbOCl_3$ and $TaOCl_3$, the niobates M'Nb $O_3$ and M'TaO$_3$ wherein M' represents lithium, sodium, potassium, cesium or an ammonium cation.

The different constituents (metal precursor, anionic ligands Z, Z', Z'', neutral ligands L and L', salts $A^+X^-$, hydrogen peroxide) may be introduced in any other, in amounts equal to or different from the stoichiometrical ratios indicated in formulas [I] to [IV], in aqueus, aquoorganic or organic solution.

III REACTIVITY OF THE COMPLEXES [I] to [IV]

One of the most characteristic properties of the complexes is that they can transfer oxygen stoichiometrically to a hydrocarbon substrate which may be an olefin or an aliphatic or aromatic saturated hydrocarbon.

When the substrate is an olefin, the product mainly obtained is the corresponding epoxide, according to equation (1)

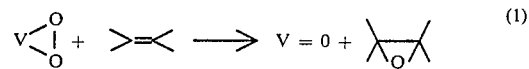
(1)

In the case where the substrate is an alkane or an aromatic hydrocarbon, the product mainly obtained is the corresponding alcohol or phenol, according to the equation:

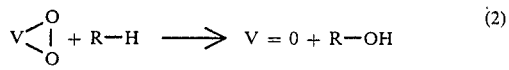
(2)

wherein R represents anyl aliphatic or aromatic hydrocarbon radical.

Another characterizing property of these complexes is that they can be regenerated from their corresponding reduced forms by addition or a compound of peroxidic character such as hydrogen peroxide or an organic hydroperoxide, according to equations (3) and (4):

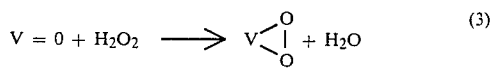
(3)

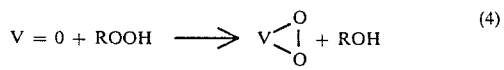
(4)

The peroxidic complexes may be used accordingly either as reactants for olefins epoxidation or hydrocarbons hydroxylation according to the equations (1) and (2) or as oxidation catalysts, the ultimate oxidizing agent being hydrogen peroxide or hydroperoxides.

(1) OLEFINS EPOXIDATION

Complexes [I] to [IV] are particularly reactive with respect to olefins by converting them mainly to the corresponding epoxides. However, the formed expoxides are liable in turn to be further oxidized to carbonyl derivatives resulting from the oxidizing splitting of the expoxide. In order to limit as much as possible this further reaction of oxidizing degradation of the epoxide, it is often advantageous to proceed in the presence of one or more equivalents of the ligand L or L' having electrodonor properties, such as above defined.

Examples of olefins or olefinic compounds liable to be epoxidized by complexes [I] to [IV], are: ethylene, propylene, isobutene, 1-butene, cis and trans 2-butenes, 1-pentene, 2-pentenes, 2-methyl 2-butene, 2-methyl 1-butene, cyclopentene, 1-hexene, 2-hexene, 3-hexene, 2-methyl 2-pentene, 2-methyl 1-pentene, tetramethylethylene, cyclohexene, cycloheptene, 2,4,4-trimethyl 1-pentene and 2-pentene, methyl-hexenes, 1,2 and 3-octanes, cyclooctene, 1,2,3 and 4-dodecenes, cyclododecene, isobutene dimers, trimers and polymers, butadiene and butadiene oligomers, limonene, cis and trans stilbenes, styrene, α-methyl styrene, cis and trans β-methylstyrenes, propylene dimers, trimers and oligomers, unsaturated glyacids such as soya oil and natural vegetal oils as well as the unsaturated oleic, linolenic, balicic, erucic, ricinoleic, etc . . . fatty acids or esters.

(2) HYDROXYLATION OF ALIPHATIC AND AROMATIC HYDROCARBONS

One of the remarkable properties of complexes [I] to [IV] according to the invention is their capacity to transfer oxygen to saturated or aromatic hydrocarbons so as to form the corresponding alcohols or phenols.

The hydrocarbons liable to be sujected to hydroxylation according to the process of the invention may be selected from the group consisting of:

linear or branched saturated aliphatic hydrocarbons of the general formula $$C_nH_{2n+2}$$

wherein n is an integer from 1 to 30. Examples are methane, ethane, propane, butane and isobutane, pentanes, hexanes, heptanes, octanes, nonanes, decanes, undecanes, tetradecanes, linear or branched hexadecanes, etc . . .

alicyclic substituted or unsubstituted hydrocarbons containing 3 to 20 carbon atoms per molecule. Examples are cyclobutane, cyclopentane, cyclohexane, cycloheptane, cyclooctane, cyclododecane, methyl, dimethyl, trimethyl, ethyl, diethyl, isopropyl and tert-buty cyclopentanes and cyclohexanes.

Aromatic hydrocarbons containing at least one benzene ring with 6 carbon atoms per molecule. These aromatic hydrocarbons may have 1 to 6 benzene rings condensed, uncondensed or interconnected through saturated hydrocarbon chains containing for example 1 to 10 carbon atoms. The aromatic rings may be unsubstituted or substituted with hydrocarbon groups or with a group selected from the methoxy, carboxy, hydroxy, amino, chloro, bromo, nitro, cyano, etc . . . groups.

Examples of aromatic hydrocarbons are benzene, toluene, ortho-, meta- and paraxylenes, mesitylene, durene, ethylbenzene, cumene, tert-butylbenzene, diisopropylbenzene, cymene, naphthalene, anthracene, phenanthrene, anisole, benzoic acid, phenol, acetylanilide, chlorobenzene, bromobenzene, nitrobenzene, etc . . .

It is noticeable that when the hydrocarbon is aliphatic or alicyclic, the hydroxylation is effected on the tertiary carbons preferentially to the secondary and primary carbons. For example methyl butane is preferentially hydroxylated to 2-methyl-2-butanol, cyclohexane to cyclohexanol, octane to 2,3,4-octanol. In the case where the formed alcohol is a secondary alcohol, the joined formation of a ketone is also observed, said ketone resulting from the further oxidation of the alcohol. Thus, for example, cyclohexane is oxidized by complexes [I] to [IV] to a mixture of cyclohexanol and cyclohexanone.

The hydroxylation of aromatic hydrocarbons by the above mentioned complexes is generally more easy than that of the aliphatic hydrocarbons and leads to phenols as main products. This hydroxylation is preferably effected on the positions having the greater number of electrons. For example, toluene is preferentially hydroxylated to ortho and paracresol. Benzene is hydroxylated to phenol.

IV THE USE OF THE CATALYSTS AND THE OPERATING CONDITIONS

The complexes may behave simultaneously as stoichiometrical reactants and as oxidation catalysts in the presence of an oxygen donor such as hydrogen peroxide or an organic hydroperoxide.

They may be used directly in the hydrocarbon substrate to be oxidized or in any organic solvent wherein they are soluble. Examples of solvents are:

chlorinated solvents such as methylene chloride, dichloroethane, chloroform, chlorobenzene, etc . . .

nitrated solvents such as nitromethane, nitrobenzene, etc . . .

nitriles such as acetonitrile, propionitrile, benzonitrile, etc . . .

ketones such as acetone and methyl-ethylketone basic solvents which may be the basis of L and/or L' groups as above defined, for example dimethylformamide, dimethylacetamide, N-methylpyrrolidone, hexamethylphosphorotriamide, pyridine, quinoline, pyridine N-oxide.

The complexes may be used as such in homogeneous phase. They may also be deposited on a carrier such as silica, alumina, alumino silicates, zeolites, coals, titanium oxide, quartz, etc . . .

The reaction is conducted at a temperature generally comprised, for example, between −50° and 150° C., but preferably at a temperature from 0° to +100° C.

The presence of water in the medium, although tolerable at a low concentration, may however be detrimental and may require water removal, at least to a large extent, for example by azeotropic distillation in the presence of such a solvent as, for example, benzene, toluene or xylene or by means of a drying agent or by any other equivalent means.

The reaction medium may be neutral, acid or basic. It may be advantageous, in some cases, to proceed in the presence of a Brönstedt acid in the medium, so as to increase the activity of the complexes with respect to the hydrocarbon substrates.

The acids may be carboxylic acids, for example acetic acid, propionic acid, benzoic acid, or sulfonic acids, for example methane sulfonic acid, fluorosulfonic acid or paratoluene sulfonic acid.

The Brönstedt acid to metal ratio may be, for example, from 1 to 10, but generally this ratio is about 1:1.

The oxidation of hydrocarbons substrates may be performed stoichiometrically according to equations (1) and (2).

It may also be effected catalytically, i.e. with a small amount of complex with respect to the unsaturated substrate, when operating in the presence of an oxidizing agent such as hydrogen peroxide or an organic hydroperoxide.

The complex/substrate ratio is generally comprised between $10^{-4}$ and 0.5, for example between $10^{-3}$ and $10^{-1}$.

The peroxide/substrate ratio is generally comprised between 0.1 and 10, more particularly between 0.1 and 2.

When the hydrogen peroxide is the oxidizing agent, the operation may be conducted in biphasic medium or in monophasic medium with the use of a third solvent, such, for example, as an alcohol (e.g. tert-butanol), a nitrile (e.g. acetonitrile), ketone (e.g. acetone) or an amide (e.g. dimethyl formamide).

When the organic hydroperoxide is the oxidizing agent, the operation is generally conducted in homogeneous organic phase, in one of the above defined solvents.

Preferred hydroperoxides of the general formula ROOH, are tert-butyl hydroperoxide, ethylbenzene hydroperoxide or cumene hydroperoxide.

The present invention is illustrated by the following examples:

EXAMPLE 1

Preparation of covalent complexes of type [I] of formula MO(O₂)ZLL'.

(a) Preparation of complex No. 1 (Pic) VO (O₂) (H₂O)₂
[Z = Pic (= Picolinate); M = V(vanadium); L = L' = H₂O]

4.52 g of vanadic anhydride $V_2O_5$ (50 mM) are reacted with 6.15 g of picolininc acid (50 mM) in 20 cc of hydrogen peroxide at a 30% concentration during 4 hours at 0° C., up to complete dissolution of $V_2O_5$ and formation of an orange precipitate.

The precipitate is filtered, washed several times with ether and dried under vacuum over $P_2O_5$.

12.5 g of orange complex 1 are recovered (yield = 95% molar) whose elementary, infra-red, proton MNR analysis, confirmed by X-ray crystallography, indicated formula 1

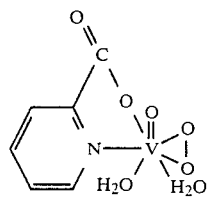

Elementary analysis = calculated for the formula V $C_6H_8NO_7$: C = 28.02; H = 3.1; N = 5.45, active oxygen = 6.22. Found: C = 28.01; H = 3.11; N = 5.44, active oxygen (by cerimetry) = 6.1.

Infrared analysis: [V=O] = 975 cm$^{-1}$, [O—O] = 935, 580, 550 cm$^{-1}$.

Preparation of complexes 2–8

The following complexes 2–8, whose list is given in Table I, are of the same type as complex 1, but differ in that two moles of water have been replaced by various vasic ligands. The following preparation methods have been used:

METHOD A: To a solution of complex 1 in water, maintained at 0° C., is added an amount of ligand L and/or L' equal to or slightly greater than the stoichiometry. The formed complex precipitates.

METHOD B: To a suspension of complex 1 in methylene chloride $CH_2Cl_2$ maintained at 0° C., is added an amount of ligand L and/or L' equal to or slightly greater than the stoichiometry. The formed complex is dissolved in methylene chloride. The obtained red solution is evaporated. The formed complex precipitates by addition of ether.

METHOD C: (Case where L is an alcohol) Complex 1 is directly dissolved in the alcohol. The concentrated solution to which the ether is added provides the desired complex.

METHOD D: The ligand is added to an equimolecular solution of $V_2O_5$ and of picolinic acid in 30% hydrogen peroxide $H_2O_2$. The obtained expected complex precipitates.

The formed complexes are of formula [I] in the case where L and L' are monodentate, and [I'] in the case where L and L' form together a single bidentate ligand:

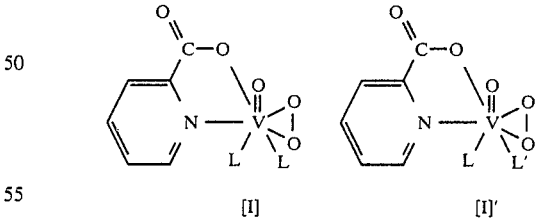

TABLE I

| No. of COMPLEX | TYPE | L | L' | METHOD | MOLAR YIELD | $\nu(V=0)$ $\nu(0—0)$cm$^{-1}$ |
|---|---|---|---|---|---|---|
| 2 | [I] | CH₃OH[1] | H₂O | C | 90% | 975–935 |
| 3 | [I] | HMPT[2] | H₂O | B | 70% | 960–950 |

TABLE I-continued

| No. of COMPLEX | TYPE | L | L' | METHOD | MOLAR YIELD | $\nu(V=O)$ $\nu(O-O)$cm$^{-1}$ |
|---|---|---|---|---|---|---|
| 4 | [I] | 4-picoline N-oxide (CH$_3$)$^{(3)}$ | H$_2$O | A | 90% | 950-945 |
| 5 | [I] | methyl isonicotinate (CO$_2$Me)$^{(4)}$ | H$_2$O | A | 45% | 975-945 |
| 6 | [I]' | methyl picolinate (C-OMe)* | | B | 50% | 975-945 |
| 7 | [I]' | 2,2'-bipyridine* | | A,D | 95% | 950-935 |
| 8 | [I]' | N,N-diethylpicolinamide (C-NEt$_2$)* | | A,B | 80% | 959-943 |

$^{(1)}$methanol
$^{(2)}$hexamethylphosphotriamide (or hexamethylphosphorotriamide)
$^{(3)}$4-picoline N—oxyde
$^{(4)}$4-pyridine-methyl carboxylate
$^{(5)}$methyl picolinate
$^{(6)}$2,2' bipyridine
$^{(7)}$N,N diethylpicolinamide
*L and L' in this occurrence form together a single bidentate ligand.

(c) Preparation of complexes 9 and 10 (Pyr) VO (O$_2$) L$_1$ L$_2$ Pyr=pyrazine-2-carboxylate.

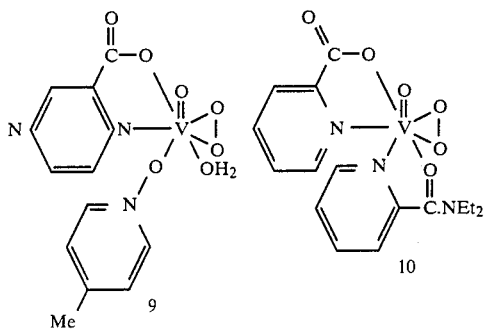

Preparation of complex 9 (Method D)

To a solution of V$_2$O$_5$ (1.82 g) and 2-pyrazine-carboxylic acid (3.4 g) in 10 cc of 30% hydrogen peroxide maintained at 0° C., are added 2.2 g of 4-picoline-N-oxide dissolved in 10 cc of water. Complex 9 is obtained by precipitation; yield: 85% molar, infrared. $\nu(V=O)=968$ cm$^{-1}$ $\nu(O-O)=948$ cm$^{-1}$.

Preparation of complex 10

To solution of V$_2$O$_5$ (1.82 g) and 2-pyrazine carboxylic acid (3.4 g) in 10 cc of 30% hydrogen peroxide, maintained at 0° C., are added 3.6 g of N,N-diethyl picolinamide.

The formed complex 10 is extracted from the solution by means of methylene chloride; yield: 45% molar. Infrared (V=O)=958 cm$^{-1}$ (O—O)=945 cm$^{-1}$.

EXAMPLE 2

Preparation of ionic complexes of type [II] of the formula [MO(O$_2$) Z Z' L]$^{-A+}$ (a) Preparation of complexes 11, 12 and 13 [(Pic)$_2$ VO (O$_2$)]$^{-}$ A$^{+}$, L (Pic=picolinate)
complex 11: A$^+$=H$^+$, L=H$_2$O
complex 12: A$^+$=H$^+$, L=HMPT
complex 13: A$^-$=P (C$_6$H$_5$)$_4^+$, L=H$_2$O Preparation of complex No. 11

4.52 g of vanadic anhydride V$_2$O$_5$ (50 mM) are reacted with 12.3 g of picolinic acid (100 mM) in 20 cc of 30% hydrogen peroxide for 4 hours at 0° C., up to complete dissolution of V$_2$O$_5$ and precipitation of a brick-red precipitate.

The precipitate is filtered, washed with ether and dried over $P_2O_5$.

17 g of brick-red complex 11 are recovered (mole yield=93%) whose elementary, infra-red, proton MNR analyses indicate the formula:

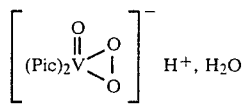 $H^+$, $H_2O$

Elementary analysis: calculated for $VC_{12} H_{10}N_2O_8$ C=39.7; H=3.03; N 7.73; Found: C=40.5; H=2.95; N=7.85.

Infrared=$\nu(V=O)=965$ cm$^{-1}$; $\nu(O-O)=935$ cm$^{-1}$.

Preparation of complex No. 12

The synthesis is the same as for complex 11 (4.52 g of $V_2O_5$ 12.3 g of picolinic acid and 20 cc of 30% $H_2O_2$) except that 13.5 g of hexamethyl phosphorotriamide (75 m moles) are further added.

The formed complex 12 is recovered by extraction in methylene chloride and precipitation with ether.

Elementary analysis: calculated for $VC_{18}H_{26}N_5O_8P$ V=9.75; C=41.3; H=5.16; N=13.38; Found: V=9.7; C=41.4; H=5.18; N=13.3.

Infrared=$(V=O)=965$ cm$^{-1}$; $(O-O)=940$ cm$^{-1}$.

Preparation of complex No. 13

To a solution of $NH_4VO_3$ (1.17 g=10 mM) and of picolinic acid (2.46 g=20 mM) in 10 cc of 30% $H_2O_2$, are added 4.2 g of tetraphenylphosphonium bromide dissolved in a minimum amount of methanol. Complex 13 precipitates and is recovered by filtration, then washed with ether; the yield is 6.5 g (92% molar).

Elementary analysis: calculated for $VC_{36}H_{30}N_2O_8P$ C=61.7; H=4.28; N=4.0; P=4.43 Found: C=61.3; H=4.21; N4.01; P=4.39.

Infrared: $(V=O)=960$ cm$^{-1}$, $(O-O)=960$ cm$^{-1}$, $(O-O)=935$ cm$^{-1}$.

The same complex has been obtained with good yields (>80% by mole) by addition of a stoichiometrical amount of tetraphenylphosphonium bromide to a solution of complex 11 or of complex 12 in water.

(b) Preparation of complexes 14, 15 and 16 of niobium of the formula $[(Pic)_2NbO (O_2)]^- A^+$.

complex 14: $A^+ = P (C_6 H_5)_4$
complex 15: $A^+ = P (C_4 H_9)_4$
complex 16: $A^+ = P (C_4 H_9) (C_6 H_5)_3$ Preparation of complex No. 14

5.04 g of potassium niobate $KNbO_2$ (20 mM) and 4.92 g of picolinic acid (40 mM) are dissolved into 30 cc of 30% hydrogen peroxide. The addition of 8.4 g of tetraphenylphosphonium bromide (20 mM), dissolved in a minimum amount of methanol, produces the precipitation of the pale yellow complex 14. After washing and drying the yield is 14 g (94% molar).

Elementary analysis: caluated for Nb $O_7C_{36}H_{28}P N_2$ C=59.6; H=3.86; N=3.86; O=15.46 Found: C=58.5; H=3.85; N=3.84; O=15.56.

Infrared: $\nu(Nb O)=850$ cm$^{-1}$ $\nu(O-O)=875$ cm$^{-1}$.

Preparation of complex No. 15

This complex has been prepared in the same manner as complex 14, but by making use of tetrabutylphosphonium bromide.

Complex 15 is extracted from the methylene chloride solution and then purified.

Molar yield=90%
Infrared: $\nu(Nb=O)=850$ cm$^{-1}$ $\nu(O-O)=875$ cm$^{-1}$

Preparation of complex No. 16

The preparation is the same as for complex 14, except for the use of butyl triphenyl phosphonium bromide. The formed complex 16 precipitates; molar yield: 85%.

Elementary analysis: calculated for Nb $O_7C_{34}H_{32}P N_2$; C=57.9; H=4.54; N=3.97; Found: C=57.2; H=4.54; N=3.92.

(c) Preparation of tantalum complexes 17 and 18 of the formula $[(Pic)_2 Ta O (O_2)]^- A^+$, L complex 17: $A^+ = P (C_6 H_5)_4$, $L=H_2O$
complex 18: $A^+ = P (CH_3) (C_6 H_5)_3$, $L=H_2O$ Preparation of complex No. 17

720 mg of tantalum chloride Ta $Cl_5$ (4 mM) are dissolved in a minimum amount of methanol. Subsequently 1 g (8 mM) of solid picolinic acid and then 10 cc of hydrogen peroxide are added. Stirring is continued up to the achievement of a homogenous solution. Then 1.68 (4 mM) of tetraphenylphosphonium bromide dissolved in water is added. The pale yellow complex 17 precipitates. The yield after filtration, washing with ether and drying over $P_2O_5$, 80% molar.

Elementary analysis: calculated for Ta $O_8C_{36}H_{30}P N_2$ C=52.04; H=3.61; N=3.37; Found: C=51.7; H=3.6; N=3.38.

Infrared: $\nu(Ta=O)=855$ cm$^{-1}$ $\nu(O-O)=835$ cm$^{-1}$.

Preparation of complex No. 18

The preparation is the same as complex 17 with the exception of the use of methyltriphenylphosphonium bromide. Molar yield: 80%.

Infrared: $\nu(Ta=O)=855$ cm$^{-1}$ $\nu(O-O)=835$ cm$^{-1}$

EXAMPLE 3

Preparation of type III ionic complexes of formula $[Z''MO (O_2) L]^- A^+$

Complex 19: $Z''$=2,6-pyridine-dicarboxylate; M=vanadium $L=H_2O$; $A=P (C_6 H_5)_4$ Complex 20: $Z''$=2,6-pyridine-dicarboxylate; M=niobium $L=H_2O$; $A=P (C_6 H_5)_4$ Preparation of complex No. 19

1.82 g of vanadic anhydride (20 mM) and 3.4 g (20 mM) of 2,6-pyridine dicarboxylic acid are dissolved at 70° C. into 10 cc of water. To the limpid pale yellow solution, cooled down to 0° C., is added 2 cc of 30% $H_2O_2$, then 8.4 g (20 mM) of tetraphenylphosphonium bromide. Complex 19 precipitates; it is filtered, washed with ether and dried; yield: 90% molar.

Infrared: $\nu(V=O)=960$ cm$^{-1}$ $\nu(O-O)=935$ cm$^{-1}$

Preparation of complex No. 20

2.52 g of potassium niobate (10 mM) and 1.7 g of dipicolinic acid (10 mM) are dissolved in 20 cc of 30% hydrogen peroxide. To the obtained limpid yellow solution are added 4.2 g of tetraphenylphosphonium bromide (10 mM). Complex 20, as precipitated, is recovered by filtration: yield: 85% molar.

Infrared: $\nu(Nb=O)=850$ cm$^{-1}$, $\nu(O-O)=875$ cm$^{-1}$

EXAMPLES 4 to 16

Stoichiometrical oxidation of olefinic substrates by peroxo vanadium, niobium and tantalum complexes of type [I] to [IV].

In a heat-insulated glass reactor is introduced under nitrogen atmosphere 0.04 mol.l$^{-1}$ of one of complexes 1 to 20 and 2 mol.l$^{-1}$ of olefinic substrate in one of the solvents indicated in Table II.

The temperature is 20° C. After 4 hours, the formed products are analyzed by gas phase chromatography and identified by the coupling of gas phase chromatography with mass spectrometry.

The results are summarized in Table II. The yields are expressed with respect to vanadium.

TABLE II

| | | STOICHIOMETRICAL OXIDATION | | |
|---|---|---|---|---|
| EXAMPLES | No. of COMPLEX | SOLVENT | SUBSTRATE | PRODUCT(S) AND MOLAR YIELD(S) % |
| 4 | 1 | CH$_3$CN |  | 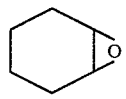 (40)    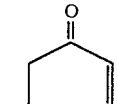 (7)     (8) |
| 5 | 12 | CH$_2$Cl$_2$ | " | 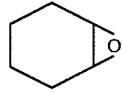 (28)    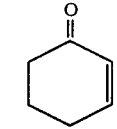 (8)     (9) |
| 6 | 12 | CH$_2$Cl$_2$ | 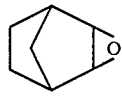 |  (40) |
| 7 | 12 | CH$_2$Cl$_2$ |  | 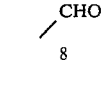 (15)     (8)    CHO 8 |
| 8 | 13 | C$_6$H$_5$NO$_2$ | " | 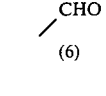 (22)     (11)    CHO (6) |
| 9 | 12 | " | 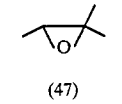 | 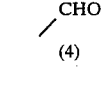 (47)    >=O (3)    CHO (4) |
| 10 | 1 | CH$_3$CN |  | 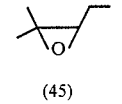 (45)    >=O (20)    CHO (20) |
| 11 | 1 | CH$_3$CN | 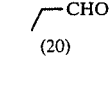 (30) |  | 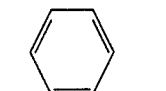 (25)    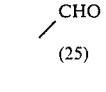 CHO (25) |

TABLE II-continued

STOICHIOMETRICAL OXIDATION

| EXAMPLES | No. of COMPLEX | SOLVENT | SUBSTRATE | PRODUCT(S) AND MOLAR YIELD(S) % |
|---|---|---|---|---|
| 12 | 12 | C₆H₅NO₂ | " | 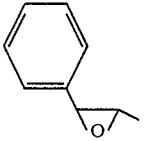 (41)    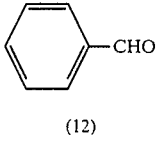 (12)    CHO (9) |
| 13 | 13 | C₆H₅NO₂ | " | (27)    (11)    CHO (10) |
| 14 | 8 | CH₂Cl₂ | " | (25)    (8)    CHO (7) |
| 15 | 14 | C₆H₅NO₂ | " | (7)    (25)    CHO (24) |
| 16 | 17 | " | " | (7)    (11)    CHO (10) |

EXAMPLES 17 to 24

Stoichiometrical hydroxylation of aromatic hydrocarbons.

In a heat-insulated glass reactor there is introduced, under nitrogen atmosphere, 0.04 mol.l$^{-1}$ of one of complexes 1 to 20 and 2 mol.l$^{-1}$ of aromatic hydrocarbon substrate in one of the solvents mentioned in Table III.

The temperature is 20° C. After 4 hours, the formed products are analyzed by gas phase chromatography and identified by the coupling gas phase chromatography—mass spectrometry.

The obtained results are summarized in Table III. The yields are expressed with respect to vanadium.

TABLE III

HYDROXYLATION OF AROMATIC HYDROCARBONS

| EXAMPLE | No. of COMPLEX | SOLVENT | SUBSTRATE | PRODUCT (S) | MOLAR YIELD % |
|---|---|---|---|---|---|
| 17 | 1 | CH₃CN | Benzene | Phenol | (60) |
| 18 | 4 | " | " | " | (55) |
| 19 | 6 | " | " | " | (30) |
| 20 | 11 | " | " | " | (43) |
| 21 | 12 | " | " | " | (30) |
| 22 | 8 | " | " | " | (25) |
| 23 | 1 | " | Toluene | o-cresol (24) | p + m cresol (26) |
| 24 | 11 | " | " | o-cresol (8) | p + m cresol (14) |

EXAMPLES 25 to 29

Stoichiometrical hydroxylation of saturated hydrocarbons.

In a heat-insulated reactor is introduced, under nitrogen atmosphere, 0.04 mol.l$^{-1}$ of one of complexes 1 to 20 and 2 mol.l−1 of aliphatic hydrocarbon substrate in one of the solvents indicated in Table IV.

The temperature is 20° C. After 4 hours, the formed products are analyzed by gas chromatography and identified by coupling of gas phase chromatography with mass spectrometry.

TABLE IV

HYDROXYLATION OF ALKANES

| EXAMPLES | No. of COMPLEX | SOLVENT | SUBSTRATE | PRODUCT(S) and MOLAR YIELD % | | |
|---|---|---|---|---|---|---|
| 25 | 1 | CH$_3$CN | Cyclohexane | Cyclohexanol (18) | cyclohexanone (8) | |
| 26 | 11 | CH$_3$CN | " | Cyclohexanol (8) | cyclohexanone (4) | |
| 27 | 1 | CH$_3$CN CH$_2$Cl$_2$ | Isobutane | tert-butanol (25) | | |
| 28 | 1 | CH$_3$CN | Adamantane | 1-adamantanol (20) | | |
| 29 | 1 | | n-octane | 2-octanone (6) | 3-octanone (3) | 4-octanone (4) |
| | | | | 2-octanol (3) | 3-octanol (3) | 4-octanol (2) |

EXAMPLES 30 and 31

Catalytic hydroxylation of benzene to phenol by means of hydrogen peroxide.

In a heat-insulated and stirred reactor, provided with a cooler, there is introduced 100 ml of benzene, then 0.1 m.mole of catalyst. The reactor is brought to benzene reflux at 80° C. Hydrogen peroxide at a 70% concentration (10 ml) is then introduced dropwise so as to maintain a very small aqueous phase, taking into account the water removal by azeotropic distillation.

The amount of produced phenol is determined by gas phase chromotagraphy.

| Ex. | Catalyst No. of Complex | Phenol m mole | Reaction time |
|---|---|---|---|
| 30 | 19 | 0.5 | 0,5 h |
| 31 | 5 | 1.5 | 1 h |

EXAMPLES 32 to 36

Catalytic hydroxylation of benzene to phenol by means of tert-butyl hydroperoxide.

In a heat-insulated reactor, maintained at 60° C., are introduced 20 ml of benzene, 0.1 m mole of catalyst and 20 m moles of tert-butyl hydroperoxide.

The amount of phenol produced is determined by gas phase chromatography and the amount of the unconverted hydroperoxide by iodometry.

| EXAMPLES | No. of COMPLEX | PHENOL (m moles) | TIME |
|---|---|---|---|
| 32 | 19 | 0.3 | 0,5 h |
| 33 | 12 | 0.4 | " |
| 34 | 11 | 0.4 | " |
| 35 | 5 | 0.5 | " |
| 36 | 1 | 0.4 | " |

What is claimed is:

1. In a process comprising catalytically hydroxylating an aromatic hydrocarbon with hydrogen peroxide or an organic hydroperoxide, to produce a phenolic compound, the improvement wherein the catalyst is a vanadium or niobium or tantalum peroxidic complex selected from the general formulas I to IV

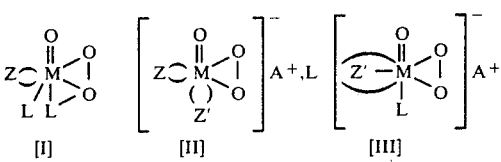

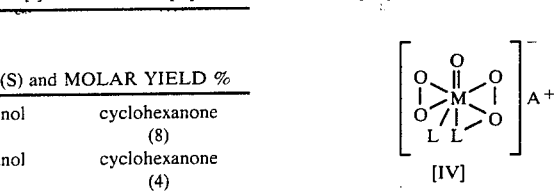

wherein M is vanadium, niobium or tantalum, Z and Z', identical or different, are mono or polyaromatic nitrogenous heterocyclic substituted or not by at least one Y group selected from the nitro, halogen, carboxylate, carboxyamide and hydroxyl groups, Z" is a dianionic tridentate ligand derived from 2,6-pyridine dicarboxylic acid substituted by one or more Y groups selected from the alkyl, aryl, alkyloxy, aryloxy, nitro, halogen, carboxylate, carboxyamide or hydroxyl groups, L and L' identical or different being each a molecule of water or alcohol or a mono or bidentate ligand of electrodonor character, (or forming together a bidentate ligand), said ligand being selected from the group constituted of
  (a) an aromatic amine
  (b) a linear or cyclic tertiary amide
  (c) a phosphoramide
  (d) an aliphatic or aromatic amine oxide
  (e) a phosphine, arsine or stibine oxide,
A being or proton or a cation or a cationic group selected from:
  (a) an alkali metal
  (b) a quaternary ammonium group
  (c) a phosphonium or arsonium quaternary group.

2. The process according to claim 1, wherein Z and Z', identical or different, are selected from the group consisting of picolinic acid, 2-pyrazine carboxylic acid, 2-quinoline carboxylic acid, 2,4-pyridine dicarboxylic acid and 2,5-pyridine dicarboxylic acid.

3. The process according to claim 1, wherein Z" is 2,6-pyridine dicarboxylic acid.

4. The process according to claim 1, wherein L and L', identical or different, are each a molecule of water or alcohol, or a mono or bidendate ligand of electrodonor character selected from the group consisting of pyridine, quinoline, acridine, 2,3- and 4-picolines, methyl picolinate, 2,2'-bipyridine, orthophenantroline, dimethylformamide, dimethylacetamide, diethylformamide, N,N-diethylpicolinamide, N-methylpyrrolidone, hexamethylphosphotriamide, N-methylmorpholine oxide, pyridine oxide, 2,3- and 4-picoline oxides, quinoline oxide, triphenylphosphine oxide, triphenylarsine oxide.

5. The process according to claim 1, where $A^+$ is a proton or a cation selected from the group consisting of an alkali metal and a quaternary ammonium, phosphonium or arsonium group.

6. The process according to claim 1, the reaction being effected the molar ratio complex/ hydrocarbon substrate being comprised between $10^{-4}$ and 0.5.

7. The process according to claim 1, wherein the aromatic hydrocarbon is benzene.

8. The process according to claim 1, wherein the aromatic hydrocarbon is toluene.

9. The process according to claim 2, wherein the aromatic hydrocarbon is benzene or toluene.

10. The process according to claim 3, wherein the aromatic hydrocarbon is benzene or toluene.

11. The process according to claim 4, wherein the aromatic hydrocarbon is benzene or toluene.

12. The process according to claim 5, wherein the aromatic hydrocarbon is benzene or toluene.

13. A process according to claim 1 wherein M is vanadium.

14. A process according to claim 1 wherein M is niobium.

15. A process according to claim 1 wherein M is tantalum.

16. A process according to claim 13 wherein the aromatic hydrocarbon is benzene or toluene.

17. A process according to claim 14 wherein the aromatic hydrocarbon is benzene or toluene.

18. A process according to claim 15 wherein the aromatic hydrocarbon is benzene or toluene.

* * * * *